United States Patent [19]

Cerami

[11] 4,436,094
[45] Mar. 13, 1984

[54] MONITOR FOR CONTINUOUS IN VIVO MEASUREMENT OF GLUCOSE CONCENTRATION

[75] Inventor: Anthony Cerami, New York, N.Y.

[73] Assignee: Evreka, Inc., Bergenfield, N.J.

[21] Appl. No.: 343,128

[22] Filed: Jan. 27, 1982

Related U.S. Application Data

[63] Continuation-in-part of Ser. No. 241,991, Mar. 9, 1981, Pat. No. 4,330,299.

[51] Int. Cl.³ .................. G01N 33/66; G01N 27/30
[52] U.S. Cl. ................................ 128/635; 204/1 T; 204/403; 204/415; 436/95; 436/827
[58] Field of Search ............... 128/635; 204/195 B, 204/1 T, 403, 415; 23/230 B, 901; 436/827

[56] References Cited

U.S. PATENT DOCUMENTS 3,615,228  5/1971  Thiegs ........................... 23/230 B
4,240,438  12/1980  Updike ............................ 128/635
4,340,458  7/1982  Lerner ....................... 204/195 B X

FOREIGN PATENT DOCUMENTS

WO81/0035-
41  2/1981  PCT Int'l Appl. .

OTHER PUBLICATIONS

Cerami, et al., "A Glucose-Controlled Insulin Delivery System . . . Lectin", *Science*, vol. 206, No. 4423, pp. 1190–1191, (1979).

Borrebaeck, C. et al., "A Binding Assay of Carbohydrates and Glycoproteins Using a Lectin Electrode", *Chem. Abstr.*, 92:300 Abstract No. 193916j.

*Primary Examiner*—Sidney Marantz
*Attorney, Agent, or Firm*—David A. Jackson; Daniel H. Bobis

[57] ABSTRACT

A method for the continuous, in vivo measurement of glucose concentration in animal body fluids such as blood, comprises implanting in the body, in registry with the system for the body fluid, a glucose monitor adapted to measure the concentration of glucose as a function of changes in such electrical charge. The glucose monitor includes an electrode with an electrical charge-transfer medium comprising a reversible complex of a binding macromolecular component and a charge-bearing carbohydrate component. The electrode includes a selectively permeable membrane permitting the ingress and egress of the body fluid. In operation, glucose present in the body fluid displaces the charge-bearing carbohydrate, which then participates in the electrical activity of the electrode so that a measurable change in electrical activity can be observed when the electrode is connected to an appropriate current-responsive meter. Preferably, the macromolecular component comprises one or more lectins, and the charge-bearing carbohydrate component may be one or more of the sugars for which testing is desired.

30 Claims, 1 Drawing Figure

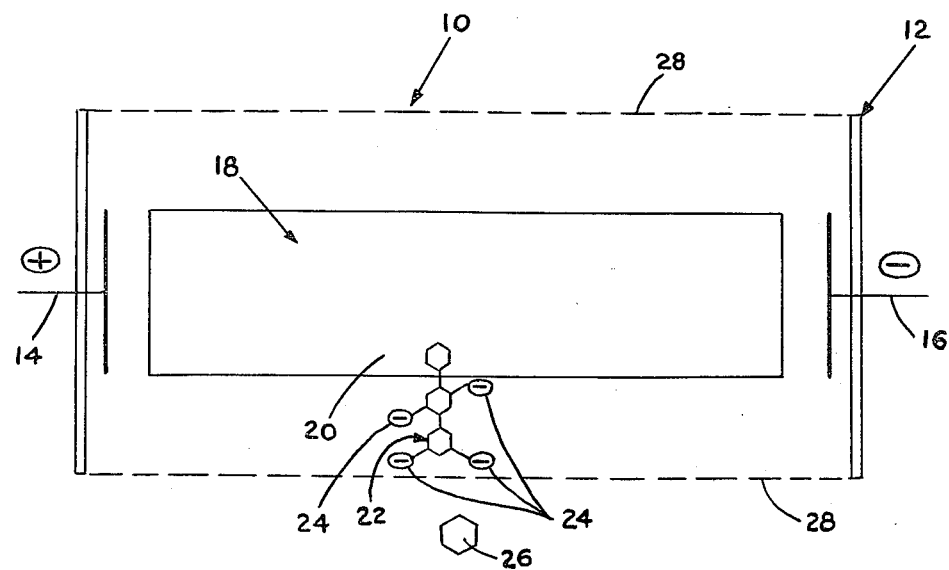

MONITOR FOR CONTINUOUS IN VIVO MEASUREMENT OF GLUCOSE CONCENTRATION

CROSS-REFERENCE TO RELATED APPLICATIONS

The present Application is a Continuation-In-Part of copending Application Ser. No. 241,991, filed Mar. 9, 1981, by the inventor herein, now U.S. Pat. No. 4,330,299, issued May 18, 1982.

BACKGROUND OF THE INVENTION

1. Field of the Invention

The present invention relates to an apparatus and associated method for the continuous, in vivo measurement of glucose in animal body fluids.

2. Description of the Prior Art

The detection and measurement of glucose in body fluids, such as blood, urine and cerebro-spinal fluid, provides information crucial to a proper assessment of the functions of the body. While hypo- and hyperglycemic conditions, which result from abnormal variations in blood glucose level, require prompt and accurate measurement in instances such as the administration of emergency medical attention to patients exhibiting these conditions, the need for an ongoing measurement of blood glucose levels is frequently necessary for patients with continuing diabetic conditions.

A variety of apparatus, including indwelling probes have been developed and tried, however these devices have proved wanting for specificity, and suffer from interference from other biological compounds. For example, Colton et al., Transplantation and Clinical Immunology, Volume X, Pages 165–173, Amsterdam (1978), disclose a system including an electronic glucose sensor, an insulin reservoir and pump, and electronics connecting the two. In this system, the sensor responds to rising glucose levels, and instructs the reservoir and pump to automatically dispense an appropriate quantity of insulin into the bloodstream. The sensor utilizes a platinum electrode catalyst for the purpose of oxidizing glucose therein. The use of the catalyst, however, results in reduced specificity of the electrodes, that exhibit interference with other metabolites, and resulting unreliability.

Soeldner et al., NIH Publication No. 76-854 (1976), at Pages 267–277, propose a glucose-sensitive implant electrode, that utilizes an immobilized quantity of the enzyme glucose oxidase, that by its action on available glucose in the blood stimulates an ion exchange that causes a corresponding differential incurrent that may be sensed and reported by the electrode. The mechanism of glucose oxidase activity with body fluid, it also used in a corresponding in vitro test, where the formation of hydrogen peroxide by the reaction of the enzyme, in the presence of a leuco dye, results in a visible color reaction. The invivo system of Soeldner et al. is deficient in that the enzyme glucose oxidase is unstable in this environment, and therefore is an unreliable determinant of glucose concentrations.

In my copending Application Ser. No. 241,991, the pertinent disclosure of which is incorporated herein by reference, a method and corresponding article for in vitro glucose monitoring is disclosed, which relies upon a glucose indicator comprising a reversible complex of a carbohydrate component, a binding macromolecular component and an indicator element bound to one of the components. In particular, the system utilizes a macromolecular component that may include carbohydrate-binding proteins such as lectins, that exhibit specific binding affinity for particular carbohydrates, and a continuum of carbohydrate oligomers of differing size, to offer a graded response to glucose concentrations. The disclosed system and method were primarily devised for use in in vitro monitoring wherein a sample of body fluid is abstracted and tested periodically to determine glucose levels therein.

A need is believed to exist for the development of an effective indwelling glucose monitor, that can offer continuous, in vivo-derived data regarding the dynamic condition of body fluid in terms of glucose concentration.

SUMMARY OF THE INVENTION

Accordingly, a method for continuously measuring glucose in vivo, in animal body fluids, comprises implanting an indwelling glucose monitor having a variable electrical charge, within the body of the animal in registry with the system of body fluid to be monitored. The glucose monitor is adapted to measure the concentration of the glucose as a function of changes in its electrical charge, and includes a charge transfer medium comprising a reversible complex of a binding macromoleculor component, and an electrical charge-bearing carbohydrate component. Body fluid is capable of passing through the monitor and increases in glucose level are reflected in release of the charge-bearing carbohydrate to the electrical field of the monitor, to register a corresponding increase in the flow of the electrical charge.

The glucose monitor may comprise an electrode, having an anode and a cathode spaced apart therefrom, and the electrical charge transfer medium disposed therebetween. The incremental changes in electrical charge within the present monitor results from low level inductive effects, that may be easily measured by existing electrical diagnostic equipment, available for measurement of charge differentials of this order. The macromolecular component of the electrical charge transfer medium may be selected from carbohydrate-binding proteins such as lectins, with specific binding affinities for particular carbohydrates. Carbohydrate components may comprise one or more carbohydrate oligomers of differing size, that may have charged substituents bound thereto. In one embodiment, the subunits of the oligomer may each bear a given unit charge, so that oligomers of differing chain length will offer a charge corresponding linearly in magnitude to the number of recurring carbohydrate units.

In practice, glucose present in the body fluid passing through the electrode or monitor displaces the charged carbohydrates bound to the macromolecular component, with the result that the charged carbohydrate components enter the electrical field and cause a change in the magnitude of electrical charge exhibited by the monitor.

The monitor or electrode is enclosed within a semi-permeable membrane, that is selectively permeable to glucose and the remaining fractions of the body fluid, but is impermeable to the egress of the charged carbohydrate components. In one embodiment, the membrane may possess a surface charge for the purpose of repelling the charged-bearing carbohydrate component and thereby containing same within the electrode.

Specific lectins may be utilized in association with specific carbohydrates, to test for particular sugars present in the body fluid. The electrical charge transfer medium may include a variety or continuum of lectin-carbohydrate oligomer complexes, each evidencing a variant charge magnitude, responsive to the presence of differences in the identity or concentration of the sugars present.

A glucose monitor comprising the electrode described earlier, is contemplated as part of the present invention, and may be implanted alone, or in conjunction with appropriate insulin dispensing means or the like. An appropriate current-responsive meter may be selected from equipment available in the art, and specifically calibrated to reflect precise changes in glucose concentration.

The present invention offers a simple yet accurate and reliable method and accompanying apparatus for the continuous, in vivo determination of glucose concentration in body fluids. The dissociation of the electrical charge-transfer medium is less subject to variations due to time and temperature parameters, and is therefore more reliable.

Accordingly, it is a principal object of the present invention to provide a method for continuously measuring the presence in concentration of glucose in animal body fluids.

It is a further object of the present invention to provide a method as aforesaid which yields reliable results.

It is a yet further object of the present invention to provide an indwelling glucose monitor adapted to measure glucose concentration as a function of changes in electrical charge.

It is a yet further object of the present invention to provide a glucose monitor as aforesaid, that utilizes an electrical charge-transfer medium of simple construction and reliable operation.

Other objects and advantages will become apparent to those skilled in the art from a consideration of the ensuing description which proceeds in part with reference to the following drawing.

BRIEF DESCRIPTION OF THE DRAWING

The FIGURE is a schematic plan view illustrating the possible construction of a glucose monitor in accordance with the present invention.

DETAILED DESCRIPTION

The measurement of glucose concentrations in body fluid in accordance with the present invention, makes use of an indwelling glucose monitor that resides in fluid registry with the system of the body fluid under measurement, and measures concentration of glucose as a function of changes in electrical charge. Each charge-transfer medium is disposed within the monitor that comprises a reversible complex of a binding macromolecular component, and a charge-bearing carbohydrate component that reversibly dissociates from the macromolecular component, and thereby causes a variation in the electrical activity that may be linearly related to the concentration of glucose in the body fluid.

An important element of the present invention is the binding macromolecular component. The term "macromolecular component" as utilized herein, refers primarily to molecules that evidence reversible binding capability with other micro- or macromolecules. Examples of molecules meeting the foregoing definition include natural binding proteins, enzymes, regulatory proteins and synthetically modified binding molecules, such as chemically modified proteins. Of these, the natural proteins known as lectins are preferred herein.

Lectins are carbohydrate-binding proteins of plants and animals that exhibit a variety of specificities for carbohydrates (Lis et al., Ann, Review of Biochemistry, 42, 541 (1973); I. J. Goldstein and C. E. Hayes, Adv. in Carbohydrate Chemistry and Biochemistry, Vol. 35, R. S. Tipson and D. Horton, eds. (Academic Press, New York, 1978, pp. 128–341), herein incorporated by reference). Lectins, and in particular the lectin known as Concanavalin A, a Jack Bean lectin, exhibit a natural affinity for various sugars which, more particularly, is a function of the number of saccharide subunits of the given sugar. For example, Concanavalin A, which is specific for glucose and mannose, will not bind with galactose; particularly, specificity is shown for $\alpha$-D-mannopyranose and $\alpha$-D-glycopyranose.

Other lectins, such as soybean lectins show similar specificities; thus, soybean lectins are specific fo $\beta$-D-N acetylgalactosamine and $\alpha$-D-galactose units, and wheat germ lectin is specific for $\beta$-D-N acetylglucosamine. The preferred lectin, Concanavalin A, is also observed to have an increased affinity for multiples of glucose up to 6.

The carbohydrate component preferably comprises a sugar, and includes the simple sugars or monosaccharides, as well as their low molecular weight condensation polymers, known as the oligosaccharides, that conventionally contain from two to nine monosaccharide units. Many of the sugars are naturally occurring, and may be found in animal body fluid. Particularly, a carbohydrate component may comprise glucose in the monomeric or oligomeric form; glucose oligomers may include other saccharides such as mannose and galactose, and may be either recovered from nature or synthetically prepared. The naturally occurring oligosaccharides are often associated with protein or lipid fractions, and may be utilized herein in such form.

The specific carbohydrate component useful in the present invention is chosen on the basis of its equivalence in affinity for the formation of the reversible complex with the macromolecular component, with the material or agent to be detected and measured by the indwelling monitor. Thus, for example, as the lectin Concanavalin A has an increasing affinity for glucose oligomers with greater numbers of monosaccharide units; correspondingly, this affinity would extend to concentrations of glucose in a fluid sample that would correspond in range. In particular, the corresponding range of glucose concentrations in body fluids lies within the physiological range of 10–400 mg/dl. Accordingly, a glucose indicator could be prepared with a plurality of lectin molecules, each disposed on a substrate, and reversibly associated with carbohydrate components of differing size, representing a continuum of saccharide units corresponding to the physiological range of glucose. Relatively low levels of glucose concentration would be unable to displace the higher oligomers, but would readily displace the oligomers of corresponding affinity, which in turn would permit the associated indicator element to signify the presence of glucose in that concentration. The exact operation of the reversible complex, and the electrical charge-transfer medium will be discussed hereinbelow.

The reversible complex constituting the electrical charge-transfer medium of the present invention comprises a reaction between the macromolecular component and the carbohydrate components, as generally noted above. This reaction must be reversible and non-covalent. The bonding that occurs between the respective components is caused by non-covalent forces such as hydrophobic, ionic hydrogen bonding forces and the like. Such interactions are known in the art, and their effects on molecular affinity and recognition have been described, for example, in Korolkovas et al., "Essentials of Medicinal Chemistry", pp 44–81, John Wiley & Sons, 1976, and the particular reactions of proteins and carbohydrates has been reviewed in Goldstein, I. J. ed., *Carbohydrate-Protein Interaction*, ACS Symposium Series No. 88 (1979), both incorporated herein by reference. An example of a reversible interaction is the interaction between an enzyme and its substrate or a competitive inhibitor thereof.

As described earlier in brief, the present reversible complex between the carbohydrate component and the macromolecular component operates in a state of dynamic equilibrium, as the material in the body fluid being tested for, and the carbohydrate component compete for association with the macromolecular component. In the instance where the macromolecular component is a lectin, and the material under test is glucose at certain levels of concentration, the charge-transfer medium of the glucose monitor such as that described above and schematically illustrated in the FIGURE, participates in an equilibium that arises between the glucose at the particular concentration and the reversible complex bearing a corresponding carbohydrate component, to complex with the lectin. The displacement of the electrical charge-bearing carbohydrate component of a particular reversible complex permits that carbohydrate to affect the level of electrical charge in the monitor, to signify the presence of the particular concentration of glucose. The construction and function of the glucose monitor is discussed below.

Referring now to the FIGURE, an indwelling glucose monitor is illustrated, which comprises electrode 10. Electrode 10 comprises a housing 12 with anode 14 and cathode 16 mounted inside, in spaced apart relation to each other. As the present illustration is schematic, it can be visualized that conventional means for external electrical connection can be provided to interface with anode 14 and cathode 16, to provide means for current circulation and measurement in conjunction with an appropriate source of electric current, and current metering means, not shown, which may be connected to electrode 10 in electrical series therewith.

In accordance with conventional electrode construction, a source of electrical current transfer is disposed within housing 12, to permit the passsage of charge between anode 14 and cathode 16. In the present electrode, this charge source may comprise in whole or in part, electrical charge-transfer medium 18, which, as schematically illustrated, comprises a segment of immobilized macromolecular material, such as a lectin, that is either bound to a solid substrate, or is itself polymerized and solidified. The lectin 20 may have attached thereto one or more charge-bearing carbohydrates such as illustrated at 22. Carbohydrate 22 is shown with recurring saccharide units that bear negatively charged substituents 24. Substituents 24 may comprise negatively charged moieties that may be chemically attached to the respective carbohydrate by reaction either with one or more of the hydroxyl groups of the carbohydrate, or by attachment of the moiety to the aldehyde at the reducing end thereof. Also, the charge of a given carbohydrate subunit may vary from that of other subunits, to give further differentiation and specificity to particular glucose fractions in the body fluid. In this way, further refinement of the electrical charge-transfer medium is possible, to define both quantitatively and qualitatively, the presence of particular sugars in body fluids. Further description of the preparation of the charge-bearing carbohydrate component appears later herein.

Referring further to the FIGURE, the presentation of a continuum of charge-bearing carbohydrates is possible, so that a series of carbohydrates of differing subunit number, and, correspondingly, differing magnitude of charge, may depend from the lectin base. Also, as noted above, carbohydrates of differing composition, i.e. variant saccharides, may be bound to the same lectin, to provide a wide spectrum of glucose detection. The foregoing comprise illustrations of variations of the present invention, and should not be viewed as limitative thereof.

Referring again to the FIGURE, housing 12 provides a means for the passage therethrough of the body fluid, to permit the ingress and egress of glucose, schematically illustrated and labeled 26. To this end, a membrane 28 may be provided, surrounding all or a portion of housing 12, to provide selective permeability facilitating the free movement therethrough of glucose. A variety of polymeric materials may be utilized to prepare membrane 28, and such materials may exhibit selectivity based upon differentials in porosity, as well as surface charge. In such instance, the polymeric materials may form into the membrane, bearing the desired surface charge, or the formed membrane may subsequently be treated to provide such charge thereon. Suitable polymeric materials may be selected from positively charged and negatively charged materials, as well as materials possessing both positive and a negative charge. For example, positively charged materials may comprise polyvinyl pyridine; negatively charged materials may be selected from polyacrylic acid and polyethylene terephthalate; and a polymeric material possessing a combined positive and negative charge may comprise a polystyrene sulfonate-vinylbenzyl trimethyl ammonium chloride copolymer. Naturally, the foregoing materials are merely illustrative of suitable polymers that may be utilized in preparation of membrane 28, and the invention is accordingly not limited to these specific materials, but rather encompasses those materials possessing the requisite porosity and charge capability set forth above.

Generally, and as stated earlier, the present method comprises implanting the glucose monitor for either temporary or permanent disposition within the body of the animal in question, so that the monitor is in registry with the system of body fluids to be observed. The monitor may thus be maintained indefinitely in the body, and, upon electrical connection to appropriate current generating and current measuring means, will provide a calibrated continuous indication of glucose levels. As noted earlier, the current measuring means or gauge may be appropriately calibrated, so that specific incremental variations in glucose level may be noted and appropriate remedial action taken. In such connection, the present invention may be utilized in combination with an appropriate dispensing means, for the automatic administration of an antedote such as insulin, in the instance where the present invention is applied to a diabetic condition by fluid registry with the bloodstream.

The electrical charge-transfer medium of the present invention may be prepared as follows. The particular lectin or lectins chosen for use may be fixed to a suitable insoluble support, such as cellulose, agarose, plastic, glass and the like, by either covalent bonding or non-covalent adsorption. The technique of solid state immobilization of enzymes and other proteins on resins, films, test tubes, glass beads and the like are well known (see e.g., Zaborsky, C. "*Immobilized Enzymes*", CRC Press, Cleveland, 1973; Lowe, C. R. and Dean, P.D.G., "The Chemistry of Affinity Chromatography", *Affinity Chromatography John Wiley and Sons, N.Y.*, 1974, Axen, et al., U.S. Pat. No. 3,645,852; and Kraemer, et al., U.S. Pat. No. 4,039,413). For example, the lectin may be attached to a cellulose support by activation of the support with cyanogen halide, reaction with cyanuric acid, periodate oxidation, epoxide formation, and reaction with various bifunctional reagents, such as bisoxinane, dimethyl adipimate, phenol-2, 4-disulfonyl chloride, and divinyl sulphone. Preferably, a cellulose strip is reacted with cyanogen bromide, and the thus activated cellulose strip is then incubated with Concanavalin A, and the reaction later stopped by the addition thereto of glycine.

As noted earlier, the specific carbohydrate components may be either recovered from nature or synthetically prepared. Particular carbohydrates may be prepared by, for example, limited acid hydrolysis of mannin to form oligomers of varying length which are then separable by chromatography, to recover the specific oligosaccharides.

After the carbohydrate components are recovered, they may be treated, as noted earlier, to dispose one or more charges thereon. In particular, ionic charges may be disposed on the carbohydrates by reacting appropriate substituents or moieties with either the hydroxyl groups of the carbohydrates, or the aldehyde group disposed at the reducing end of the carbohydrate. A variety of substituents having negative charges could be so introduced, as follows: $-SO_3^-$;

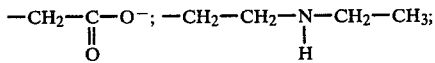

or arylhydrazines of variant negative or positive charge. Naturally, the foregoing substituents are merely illustrative of those materials that might be reacted with the carbohydrate components to achieve the ionic or charged state, as the invention encompasses all equivalent substituents that are non-toxic to the body fluid within its scope.

Once both of the components are prepared, and the macromolecular component is immobilized as desired, the carbohydrate and macromolecular components are brought in contact with each other, and establish the reversible complexes described earlier. After the reversible complexes are formed, the resulting electrical charge-transfer medium may be mounted within housing 12, together with anode 14 and cathode 16. Housing 12 may then be covered with a selectively permeable membrane 28 to complete assembly of monitor 10. As noted above, a variety of such selectively permeable membranes are already well known for use in testing equipment of this type, and include natural and synthetic resinous materials evidencing pore size, electrical charge, etc., condusive to this application.

As the present monitor will be required to operate in fluid media containing a variety of ions other than those that exist or may be formed by the action of the present charge transfer medium, one or more reference electrodes may be appropriately linked to the monitor for the purpose of detecting ions that are unrelated to the function of the monitor. For example, such electrodes may sense the presence of inorganic ions having no relation to the level of glucose, and could provide correction to the present monitor to avoid false indication of increased glucose levels. Linkage of these reference electrodes is well known, and may be accomplished by connection in a Wheatstone Bridge arrangement or equivalent disposition, to permit the reference electrodes to provide the needed correction. The particular form of such connection does not form a part of the present invention.

The invention may be embodied in other forms or carried out in other ways without departing from the spirit or essential characteristics thereof. The present invention is therefore to be considered as in all respects illustrative and not restrictive, the scope of the invention being indicated by the appended claims, and all changes which come within the meaning and range of equivalency are intended to be embraced therein.

What is claimed is:

1. A method for the continuous in vivo measurement of glucose concentration in animal body fluids comprising:
   A. preparing an indwelling glucose monitor adapted to electrically sense variations in the concentration of said glucose in said body fluid, said glucose monitor including a charge-transfer medium comprising a reversible complex of a binding macromolecular component, and a charge-bearing carbohydrate component, said reversible complex reacting with said glucose to change the level of electrical charge sensed by said glucose monitor;
   B. placing said glucose monitor in fluid registry with the system of body fluid to be monitored;
   C. maintaining said glucose monitor in fluid registry with said system for a period of time sufficient for said body fluid to permeate said glucose monitor, and for any glucose present in said body fluid to react with said reversible complex; and
   D. measuring the level of electrical charge sensed by said glucose monitor;
   wherein said level of electrical charge varies as a function of the concentration of said glucose, and said monitor is adapted to continually measure variations therein.

2. The method of claim 1 wherein said charge-bearing carbohydrate is retained within said glucose monitor, to enable said glucose monitor to sense reductions in said glucose concentration, and to perform said continual measurement.

3. The method of claim 1 wherein said glucose monitor comprises an electrode having an anode, a cathode spaced apart therefrom, and said electrical charge-transfer medium is disposed therebetween.

4. The method of claim 1 wherein, in accordance with Step B, said glucose monitor is implanted within the body of said animal.

5. The method of claim 4 wherein said glucose monitor is permanently maintained in fluid registry with said system, and said monitor continually measures variations in the concentration of said glucose.

6. The method of claim 1 wherein said charge-bearing carbohydrate component has bound thereto, at least one ionic substituent.

7. The method of claim 6 wherein said ionic substituent is selected from the group consisting of —SO₃⁻,

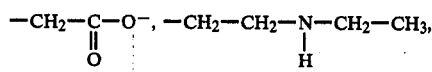

arylhydrazines having electrically charged substituents, and mixtures thereof.

8. The method of claims 1, 4 or 5 wherein said glucose concentrations is measured with reference to a current-responsive meter calibrated for such purpose.

9. The method of claims 1, 2, 4 or 3 wherein said charge-bearing carbohydrate component is retained within said monitor by a selectively permeable membrane.

10. The method of claims 1, 2, 4 or 3 wherein said binding macromolecular component comprises a binding protein, said charge-bearing carbohydrate component comprises a sugar having an ionic charge disposed thereon, said sugar selected from the group consisting of monosaccharides, oligosaccharides, and mixtures thereof.

11. The method of claim 10 wherein said binding macromolecular component is fixedly attached to an inert, insoluble substance, and said charge-bearing carbohydrate component is bound thereto in reversible complex.

12. The method of claim 10 wherein said charge-bearing carbohydrate component has bound thereto, at least one ionic substituent.

13. The method of claim 12 wherein said ionic substituent is selected from the group consisting of —SO₃⁻, 1

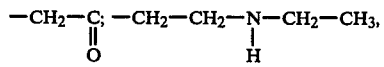

arylhydrazines having electrically charged substituents, and mixtures thereof.

14. A glucose monitor for the continuous, in vivo measurement of glucose concentration in animal body fluids comprising:
  A. an electrode adapted to electrically sense variations in the concentration of said glucose in said body fluid;
  B. said electrode including a charge-transfer medium comprising a reversible complex of a binding macromolecular component, and a charge-bearing carbohydrate component;
  C. said reversible complex adapted to react with said glucose to change the level of electrical charge sensed by said electrode, to thereby indicate corresponding variations in said glucose concentration.

15. The monitor of claim 14 wherein said binding macromolecular component comprises one or more lectins, and said charge-bearing carbohydrate component, comprises monosaccharides and oligosaccharides containing a material selected from the group consisting of glucose, mannose, and mixtures thereof.

16. The monitor of claim 15 wherein said binding macromolecular component comprises Concanavalin A, and said oligosaccharides contain up to about 6 monosaccharide units.

17. The monitor of claim 14 wherein said charge-bearing carbohydrate component comprises a sugar having one or more reactive sites thereof bound to an ionic substituent, said sugar selected from the group consisting of monosaccharides, oligosaccharides, and mixtures thereof.

18. The monitor of claim 17 wherein said charge-bearing carbohydrate component comprises a sugar having one or more reactive sites thereof bound to an ionic substituent, said sugar selected from the group consisting of monosaccharides, oligosaccharides, and mixtures thereof.

19. The monitor of claim 17 wherein said ionic substituent is selected from the group consisting of —SO₃⁻,

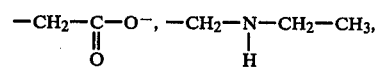

arylhydrazines having electrically charged substituents, and mixtures thereof.

20. The monitor of claim 14 wherein said electrode comprises:
  A. an electrode housing;
  B. an anode and a cathode mounted in said housing and spaced apart from each other;
  C. said charge-transfer material disposed between said anode and said cathode.

21. The monitor of claim 20 wherein said electrode is enclosed within a membrane selectively permeable to said body fluid, said membrane being permeable to said glucose, but impermeable to said charge-bearing carbohydrate.

22. The monitor of claim 21 wherein said selectively permeable membrane is porous, and defines a pore size limiting passage therethrough to said body fluid, and said glucose.

23. The monitor of claim 22 wherein said selectively permeable membrane defines a surface charge thereon, to prevent the egress from said electrode, of said charge-bearing carbohydrate.

24. The monitor of claims 14, 20 or 21 wherein said binding macromolecular component is selected from the group consisting of natural binding proteins, synthetic binding proteins and mixtures thereof.

25. The monitor of claim 24 wherein said charge-bearing carbohydrate component comprises a sugar having one or more reactive sites thereof bound to an ionic substituent, said sugar selected from the group consisting of monosaccharides, oligosaccharides, and mixtures thereof.

26. The monitor of claim 25 wherein said ionic substituent is selected from the group consisting of —SO₃⁻,

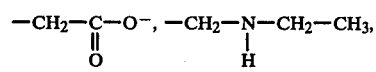

arylhydrazines having electrically charged substituents, and mixtures thereof.

27. The monitor of claim 21 wherein said charge-bearing carbohydrate component comprises a sugar having one or more reactive sites thereof bound to an ionic substituent, said sugar selected from the group consisting of monosaccharides, oligosaccharides, and mixtures thereof.

28. The monitor of claims 14, 20 or 21 wherein said reversible complex is affixed to an inert, insoluble substrate.

29. The monitor of claim 28 wherein said substrate is prepared from a material selected from the group consisting of natural and synthetic resins, ceramic materials, and mixtures thereof.

30. The monitor of claim 29 wherein said substrate is prepared from a material selected from the group consisting of cellulose, vinyl resins, glass and mixtures thereof.

* * * * *